United States Patent
Ashrafuzzaman (10) Patent No.: US 12,227,748 B1
(45) Date of Patent: Feb. 18, 2025

(54) APTAMERS FOR BINDING TO A MEMBRANE-BASED LIPID

(71) Applicant: KING SAUD UNIVERSITY, Riyadh (SA)

(72) Inventor: Md. Ashrafuzzaman, Riyadh (SA)

(73) Assignee: KING SAUD UNIVERSITY, Riyadh (SA)

(*) Notice: Subject to any disclaimer, the term of this patent is extended or adjusted under 35 U.S.C. 154(b) by 0 days.

(21) Appl. No.: 18/646,631

(22) Filed: Apr. 25, 2024

(51) Int. Cl.
*C12N 15/115* (2010.01)
*A61K 31/7088* (2006.01)
(Continued)

(52) U.S. Cl.
CPC ........ *C12N 15/115* (2013.01); *A61K 31/7088* (2013.01); *C12Q 1/025* (2013.01);
(Continued)

(58) Field of Classification Search
CPC .............. C12N 15/115; C12N 2310/16; A61K 31/7088; C12Q 1/025; C12Q 1/70; C12Q 2600/136
See application file for complete search history.

(56) References Cited

U.S. PATENT DOCUMENTS 8,484,010 B2   7/2013   Tuszynski et al.
8,709,483 B2   4/2014   Farokhzak et al.
(Continued)

FOREIGN PATENT DOCUMENTS

CN   111505284 A   8/2020
CN   111693712 A   9/2020
(Continued)

OTHER PUBLICATIONS

Ashrafuzzaman (et al. 2013. A Computationally Designed DNA Aptamer Template with Specific Binding to Phosphatidylserine. Nuc. Ac. Ther. 23[6]:418-426 (Year: 2013).*
(Continued)

*Primary Examiner* — Kimberly Chong
*Assistant Examiner* — Ruth Sophia Arieti
(74) *Attorney, Agent, or Firm* — Nath, Goldberg & Meyer; Joshua B. Goldberg (57) ABSTRACT

A lipid-binding drug for binding to a membrane-based or membrane lipid comprises at least one aptamer having a sequence selected from the group consisting of GGCGGCAAAAAAAAAA (SEQ ID NO: 1), GGCGGCAAAAAAAAAAA (SEQ ID NO: 2), GGCGGCAAAAAAAAAAAA (SEQ ID NO: 3), GGCGGCAAAAAAAAAAAAA (SEQ ID NO: 4), GGCGGCGGGGGGGGGG (SEQ ID NO: 5), GGCGGCGGGGGGGGGGG (SEQ ID NO: 6), GGCGGCGGGGGGGGGGGG (SEQ ID NO: 7), GGCGGCGGGGGGGGGGGGG (SEQ ID NO: 8), CAAAAGGAGCAAAAAAAAAAAAAAAAAAAAAAA (SEQ ID NO: 9) CAAAAGGAGCAAAAAAAAAA-AAAAAAAAAAAAA (SEQ ID NO: 10), CAAAAGGAGCAAAAAAAAAAAAAAAAAAAAA-AAA (SEQ ID NO: 11), CAAAAGGAGCAAAA-AAAAAAAAAAAAAAAAAAAA (SEQ ID NO: 12), CAAAAGGAGCGGGGGGGGGGGGGGGGGGGGG (SEQ ID NO: 13), CAAAAGGAGCGGGGGGGGG-GGGGGGGGGGGGG (SEQ ID NO: 14), CAAA-AGGAGCGGGGGGGGGGGGGGGGGGGGGGG (SEQ ID NO: 15), and CAAAAGGAGCGGGGGGGG-GGGGGGGGGGGGGGGG (SEQ ID NO: 16).

3 Claims, 4 Drawing Sheets

Specification includes a Sequence Listing.

(51) Int. Cl.
    *C12Q 1/02*           (2006.01)
    *C12Q 1/70*           (2006.01)

(52) U.S. Cl.
    CPC .......... *C12Q 1/70* (2013.01); *C12N 2310/16* (2013.01); *C12Q 2600/136* (2013.01)

(56) References Cited

U.S. PATENT DOCUMENTS

| | | | |
|---|---|---|---|
| 10,344,319 | B2 | 7/2019 | Gilboa-Geffen et al. |
| 11,001,844 | B2 * | 5/2021 | Friedland ............. C12N 15/102 |
| 2020/0332296 | A1 | 10/2020 | Kang et al. |

FOREIGN PATENT DOCUMENTS

| | | |
|---|---|---|
| KR | 10-2012-0139512 A | 12/2012 |
| KR | 10-2013-0056511 A | 5/2013 |

OTHER PUBLICATIONS

Ingolfsson (et al. 2014. Lipid Organization of the Plasma Membrane. J. Am. Chem. Soc. 136:14554â14559 (Year: 2014).*
Zhou (and Rossi. 2016. Aptamers as targeted therapeutics: current potential and challenges. Drug Discov. 16:181-202 (Year: 2016).*
Bottari (et al. 2020. Do Aptamers Always Bind? The Need for a Multifaceted Analytical Approach When Demonstrating Binding Affinity between Aptamer and Low Molecular Weight Compounds. J. Am. Chem. Soc. 142[46]:19622-19630 (Year: 2020).*
Saud (et al. 2022. The SARS-CoV2 envelope differs from host cells, exposes procoagulant lipids, and is disrupted in vivo by oral rinses. J. Lipid Res. 63[6]:100208 (Year: 2022).*
Torabi et al., "Aptamers, the bivalent agents as probes and therapies for coronavirus infections: A systematic review," Molecular and Cellular Probes, vol. 53, Oct. 2020.

* cited by examiner

APTAMERS FOR BINDING TO A MEMBRANE-BASED LIPID

INCORPORATION BY REFERENCE OF MATERIAL SUBMITTED IN COMPUTER READABLE FORM

The Applicants hereby incorporate by reference the sequence listing contained in the XML document titled 33056_75U_SEQUENCE, created Mar. 6, 2024, and having 16,000 bytes of data.

BACKGROUND

1. Field

The disclosure of the present patent application relates to aptamer-based drugs, and particularly to aptamer-based drugs for binding to membrane-based lipids.

2. Description of the Related Art

Severe acute respiratory syndrome coronavirus 2 (SARS-COV2) may trigger a fatal novel coronavirus disease 2019 (Covid-19), which has caused the ongoing pandemic humans are dealing with worldwide. Infected humans may experience three major symptoms: fever, dry cough and breath shortening, leading to almost 5% deaths among those infected.

Another respiratory illness that emerged earlier is 'Middle East Respiratory Syndrome (MERS-2012)', caused by the MERS Coronavirus (MERS-CoV).

Six species of human coronaviruses are known. One of these species is found to be subdivided into two different strains. Therefore, seven strains of human coronaviruses are presently known. Coronaviruses are enveloped positive-stranded RNA viruses that replicate in the cell cytoplasm. The nucleocapsids are delivered into host cells via cell membrane fusion of the envelopes. The viral envelope's lipid bilayer contains various phospholipids and proteins drawn from the host cell membrane.

Traditional aptamer discovery is mostly based on systematic evolution of ligands by exponential enrichment (SELEX) (Turek and Gold, 1990), where aptamer candidates are chosen from pools of candidates based on enrichment by binding with targets. Although target binding aptamers can be identified by SELEX (Turek and Gold, 1990; James, 2000; James, 2007; Hamula et al., 2006; Lao et al., 2009), this technology has disadvantages of requiring the design of extensive randomized DNA/RNA libraries, which is a complex, costly and time intensive process of selecting candidates (Keefe et al., 2010). Further, SELEX cannot account for the in situ environment of targets.

U.S. Pat. No. 8,484,010 B2 to Tuszynski and Tseng, designs aptamers by a seed-and-grow approach, optimizing entropy of a target binding with aptamer fragments by an entropic fragment based approach (EFBA). EFBA is based on a process where a first seed residue is determined by optimizing entropy of the first seed selected from a small set of aptamer building blocks (ABB) bound to the target, and then adding an additional ABB, one at a time, while maximizing the entropy of the target-aptamer complex with each addition. The EFBA does not account for binding energetics (minimum energy conformation) of the aptamer and target, particularly when the target is in a particular in situ environment such as making up or embedded in a liposome.

The envelope membrane of a virus is thought to play an important role in the final stages of infection, when new virus proteins are assembled into particles before they are released and move on to infect new cells.

Thus, aptamers useful for detecting a target, particularly in specific biological environments, such as embedded in a membrane, solving the aforementioned problems are desired.

SUMMARY

An embodiment of the present subject matter relates to a lipid-binding drug for binding to a membrane-based or membrane lipid, wherein the lipid-binding drug comprises at least one aptamer having a sequence selected from the group consisting of GGCGGCAAAAAAAAAA (SEQ ID NO: 1), GGCGGCAAAAAAAAAAA (SEQ ID NO: 2), GGCGGCAAAAAAAAAAAA (SEQ ID NO: 3), GGCGGCAAAAAAAAAAAAA (SEQ ID NO: 4), GGCGGCGGGGGGGGGG (SEQ ID NO: 5), GGCGGCGGGGGGGGGGG (SEQ ID NO: 6), GGCGGCGGGGGGGGGGGG (SEQ ID NO: 7), GGCGGGGGGGGGGGGG (SEQ ID NO: 8), CAAAAGGAGCAAAAAAAAAAAAAAAAAAAAAAA (SEQ ID NO: 9) CAAAAGGAGCAAAAAAAAA-AAAAAAAAAAAAAAA (SEQ ID NO: 10), CAA-AAGGAGCAAAAAAAAAAAAAAAAAAAAAAAAAA (SEQ ID NO: 11), CAAAAGGAGCAAAAAAAAAAA-AAAAAAAAAAAAAA (SEQ ID NO: 12), CAAAA-GGAGCGGGGGGGGGGGGGGGGGGGGGG (SEQ ID NO: 13), CAAAAGGAGCGGGGGGGGGGGGGGG-GGGGGGGG (SEQ ID NO: 14), CAAAAGGAGC-GGGGGGGGGGGGGGGGGGGGGGGG (SEQ ID NO: 15), and CAAAAGGAGCGGGGGGGGGGGGGGG-GGGGGGGGGG (SEQ ID NO:16). In an embodiment, the lipid can be selected from the group consisting of one or more of phosphatidylcholine (PC) and phosphatidylserine (PS).

Another embodiment of the present subject matter relates to a method of treating or inhibiting a coronavirus infection in a patient, the method comprising administering a therapeutically effective amount of a lipid-binding drug to a patient in need thereof, the lipid-binding drug comprising at least one aptamer having a sequence selected from the group consisting of GGCGGCAAAAAAAAAA (SEQ ID NO: 1), GGCGGCAAAAAAAAAAA (SEQ ID NO: 2), GGCGGCAAAAAAAAAAAA (SEQ ID NO: 3), GGCGGCAAAAAAAAAAAAA (SEQ ID NO: 4), GGCGGCGGGGGGGGGG (SEQ ID NO: 5), GGCGGCGGGGGGGGGGG (SEQ ID NO: 6), GGCGGCGGGGGGGGGGGG (SEQ ID NO: 7), GGCGGCGGGGGGGGGGGGG (SEQ ID NO: 8), CAAAAGGAGCAAAAAAAAAAAAAAAAAAAAAAA (SEQ ID NO: 9) CAAAAGGAGCAAAAAAAAA-AAAAAAAAAAAAAAA (SEQ ID NO: 10), CAA-AAGGAGCAAAAAAAAAAAAAAAAAAAAAAAAAA (SEQ ID NO: 11), CAAAAGGAGCAAAAAAAAAAA-AAAAAAAAAAAAAA (SEQ ID NO: 12), CAAAAGGAGGGGGGGGGGGGGGGGGGGGGGGG (SEQ ID NO: 13), CAAAAGGAGCGGGGGGGG-GGGGGGGGGGGGGGG (SEQ ID NO: 14), CAAAAGGAGCGGGGGGGGGGGGGGGGGGGGGG-GGG (SEQ ID NO: 15), and CAAAAGGAGCGGG-GGGGGGGGGGGGGGGGGGGGGGG (SEQ ID NO:16). In an embodiment, the method can comprise binding of the lipid-binding drug to a membrane-based lipid, such as a coronavirus envelope (CVE) membrane lipid. In a further embodiment, the coronavirus envelope membrane lipid can be selected from the group consisting of phosphatidylcholine (PC) and phosphatidylserine (PS). The binding of the lipid-binding drug to the coronavirus envelope membrane lipid can inhibit viral entry into a cell and, thereby, facilitate treatment of coronavirus infection.

An additional embodiment of the present subject matter relates to a method of determining efficacy of cancer treatment in a subject, the method comprising administering an effective amount of a lipid-binding drug to a subject, the lipid-binding drug comprising at least one aptamer having a sequence selected from the group consisting of GGCGGCAAAAAAAAAA (SEQ ID NO: 1), GGCGGCAAAAAAAAAAA (SEQ ID NO: 2), GGCGGCAAAAAAAAAAAA (SEQ ID NO: 3), GGCGGCAAAAAAAAAAAAA (SEQ ID NO: 4), GGCGGCGGGGGGGGGG (SEQ ID NO: 5), GGCGGCGGGGGGGGGGG (SEQ ID NO: 6), GGCGGCGGGGGGGGGGG (SEQ ID NO: 7), GGCGGGGGGGGGGGGG (SEQ ID NO: 8), CAAAAGGAGCAAAAAAAAAAAAAAAAAAAAAAA (SEQ ID NO: 9) CAAAAGGAGCAAAAAAAAAA-AAAAAAAAAAAAAA (SEQ ID NO: 10), CAA-AAGGAGCAAAAAAAAAAAAAAAAAAAAAAAAA (SEQ ID NO: 11), CAAAAGGAGCAAAAAAAAAA-AAAAAAAAAAAAAAA (SEQ ID NO: 12), CAAA-AGGAGCGGGGGGGGGGGGGGGGGGGGGGG (SEQ ID NO: 13), CAAAAGGAGCGGGGGGGGGGGGGG-GGGGGGGGGG (SEQ ID NO: 14), CAAAAGGA-GCGGGGGGGGGGGGGGGGGGGGGGGGGG (SEQ ID NO: 15), and CAAAAGGAGCGGGGGGGGGGGGGGG-GGGGGGGGGGGG (SEQ ID NO:16). In an embodiment, the method can comprise binding of the aptamer to phosphatidylserine (PS). In an embodiment, the lipid can be externalized in a lipid bilayer membrane of a cancer cell. The binding of the lipid-binding drug to the externalized lipid can be used as a marker to quantify externalized lipids and, thereby, diagnose the efficacy of the cancer drug treatment.

These and other features of the present subject matter will become readily apparent upon further review of the following specification.

BRIEF DESCRIPTION OF THE DRAWINGS

FIGS. 3A-3D are graphs of (FIG. 3A) $-k_BT \ln p_{Lip,i}$ (y-axis) for various SCI orders (i=1, 2, 3, . . . , 17) and for corresponding aptamer lengths for PC; (FIG. 3B) $-k_BT \ln p_{Lip,i}$ (y-axis) for various SCI orders (i=1, 2, 3, . . . , 17) and for corresponding aptamer lengths for PS; (FIG. 3C) for 5 ABBs including A and G (purines), and T, C, and U (pyrimidines) for PC.

Similar reference characters denote corresponding features consistently throughout the attached drawings.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as coronavirus infection.

An embodiment of the present subject matter relates to a lipid-binding drug for binding to a membrane-based or membrane lipid. The lipid-binding drug can include at least one aptamer having a sequence selected from the group consisting of GGCGGCAAAAAAAAAAA (SEQ ID NO: 1), GGCGGCAAAAAAAAAAA (SEQ ID NO: 2), GGCGGCAAAAAAAAAAAA (SEQ ID NO: 3), GGCGGCAAAAAAAAAAAAA (SEQ ID NO: 4), GGCGGCGGGGGGGGGG (SEQ ID NO: 5), GGCGGCGGGGGGGGGG (SEQ ID NO: 6), GGCGGCGGGGGGGGGG (SEQ ID NO: 7), GGCGGCGGGGGGGGGG (SEQ ID NO: 8), CAAAAGGAGCAAAAAAAAAAAAAAAAAAAAAA (SEQ ID NO: 9) CAAAAGGAGCAAAAAAAAAA-AAAAAAAAAAAAAA (SEQ ID NO: 10), CAA-AAGGAGCAAAAAAAAAAAAAAAAAAAAAAAA (SEQ ID NO: 11), CAAAAGGAGCAAAAAAAAA-AAAAAAAAAAAAAAA (SEQ ID NO: 12), CAAAAGGAGCGGGGGGGGGGGGGGGGGGGGG (SEQ ID NO: 13), CAAAAGGAGCGGGGGGG-GGGGGGGGGGGGGGG (SEQ ID NO: 14), CAA-AAGGAGCGGGGGGGGGGGGGGGGGGGGGGG (SEQ ID NO: 15), and CAAAAGGAGCGGGGGGGGG-GGGGGGGGGGGGGGG (SEQ ID NO:16). In an embodiment, the lipid is selected from at least one of the group consisting of phosphatidylcholine (PC) and phosphatidylserine (PS).

In an embodiment, the lipid is phosphatidylserine (PS) and the at least one aptamer has a sequence selected from the group consisting of GGCGGCAAAAAAAAAAA (SEQ ID NO: 1), GGCGGCAAAAAAAAAAA (SEQ ID NO: 2), GGCGGCAAAAAAAAAAA (SEQ ID NO: 3), GGCGGCAAAAAAAAAAAA (SEQ ID NO: 4), GGCGGCGGGGGGGGGG (SEQ ID NO: 5), GGCGGCGGGGGGGGGG (SEQ ID NO: 6), GGCGGCGGGGGGGGGG (SEQ ID NO: 7), and GGCGGCGGGGGGGGGG (SEQ ID NO: 8).

In another embodiment, the lipid is phosphatidylcholine (PC) and the at least one aptamer has a sequence selected from the group consisting of CAAAAGGAGCAAAAAAAA-AAAAAAAAAAAAAAAA (SEQ ID NO: 9) CAAAA-GGAGCAAAAAAAAAAAAAAAAAAAAAAAA (SEQ ID NO: 10), CAAAAGGAGCAAAAAAAAAAAAA-AAAAAAAAAAA (SEQ ID NO: 11), CAAAAGGA-GCAAAAAAAAAAAAAAAAAAAAAAAAAA (SEQ ID NO: 12), CAAAAGGAGCGGGGGGGGGGGGGGG-GGGGGGGG (SEQ ID NO: 13), CAAAAGGAGCGG-GGGGGGGGGGGGGGGGGGGG (SEQ ID NO: 14), CAAAAGGAGCGGGGGGGGGGGGGGGGGGGGGG-GGG (SEQ ID NO: 15), and CAAAAGGAGCGGGG-GGGGGGGGGGGGGGGGGGG (SEQ ID NO:16).

Envelope membranes are thought to play an important role in the final stages of infection, when new virus proteins are assembled into particles before they are released and move on to infect new cells. According to an embodiment of the present subject matter, the virus particles can be arrested by binding of the aptamer as described herein to an envelope membrane biomolecule. Binding of the aptamer to the envelope membrane biomolecule can cause alterations in the biochemical composition of the envelope and, thereby, inhibit the virus from infecting new cells. The biomolecule can include any membrane-based biomolecule, including for example, lipids, proteins, or any other membrane-based agents. In an embodiment, the biomolecule can include one or more lipids selected from the group consisting of PC and PS.

A further embodiment of the present subject matter relates to a method of treating a coronavirus infection in a patient, the method comprising administering a therapeutically effective amount of a lipid-binding drug to a patient in need thereof, the lipid-binding drug comprising at least one aptamer having a sequence selected from the group consisting of GGCGGCAAAAAAAAAAA (SEQ ID NO: 1), GGCGGCAAAAAAAAAAA (SEQ ID NO: 2), GGCGGCAAAAAAAAAAAA (SEQ ID NO: 3), GGCGGCAAAAAAAAAAAAA (SEQ ID NO: 4), GGCGGCGGGGGGGGGG (SEQ ID NO: 5), GGCGGCGGGGGGGGGG (SEQ ID NO: 6), GGCGGCGGGGGGGGGG (SEQ ID NO: 7), GGCGGCGGGGGGGGGG (SEQ ID NO: 8), CAAAAGGAGCAAAAAAAAAAAAAAAAAAAAAA (SEQ ID NO: 9) CAAAAGGAGCAAAAAAAAA-AAAAAAAAAAAAAAA (SEQ ID NO: 10), CAAA-AGGAGCAAAAAAAAAAAAAAAAAAAAAAAA (SEQ ID NO: 11), CAAAAGGAGCAAAAAAAAA-AAAAAAAAAAAAAAAA (SEQ ID NO: 12), CAAAA-GGAGCGGGGGGGGGGGGGGGGGGGGGGG (SEQ ID NO: 13), CAAAAGGAGCGGGGGGGGGGGGGGGGG-GGGGGGGG (SEQ ID NO: 14), CAAAAGG-AGCGGGGGGGGGGGGGGGGGGGGGGGGGG (SEQ ID NO: 15), and CAAAAGGAGCGGGGGGGGGGGGG-GGGGGGGGGGGGG (SEQ ID NO:16).

In an embodiment, the method can comprise binding of the lipid-binding drug to a membrane-based lipid. In an additional embodiment, the membrane-based lipid can be a coronavirus envelope membrane lipid. In a further embodiment, the coronavirus envelope membrane lipid can be selected from the group consisting of phosphatidylcholine (PC) and phosphatidylserine (PS). The binding of the lipid-binding drug to the membrane-based lipid can inhibit viral entry into a cell and, thereby, facilitate treatment of coronavirus infection in the patient.

The envelope membrane of a virus is believed to play an important role in the final stages of infection, when new virus proteins are assembled into particles before they are released and move on to infect new cells. According to an embodiment of the present subject matter, the virus particles can be arrested by binding of the aptamer to a viral envelope membrane biomolecule. Binding of the aptamer to the viral envelope membrane biomolecule can cause alterations in the biochemical composition of the envelope and, thereby, inhibit the virus from infecting new cells. The viral envelope membrane biomolecule can include any membrane-based lipid, including, by way of non-limiting example, lipids, proteins or any other membrane-based agents. In an embodiment, the envelope membrane biomolecule can include one or more lipids selected from the group consisting of phosphatidylcholine (PC) and phosphatidylserine (PS).

According to an embodiment, aptamers for binding to a target biomolecule (TB) can be determined based on a screened Coulomb interactions technique or charge-based interactions of each aptamer building block (ABB) or nucleotide and the target biomolecule (TB), as described in U.S. Pat. No. 10,916,330, the subject matter of which is incorporated by reference herein in its entirety.

In an embodiment, the target biomolecule (TB) can be a lipid selected from the group consisting of phosphatidylcholine (PC) and phosphatidylserine (PS). Optimal ABBs are associated with minimum binding energy conditions. When the aptamer approaches a target biomolecule (TB), the respective individual charges on each molecular site polarize each other. The total energy in a two body (aptamer and target) system can be calculated as screened Coulomb interactions (SCIs) arising among many charge interactions. The resultant binding energy is the sum of energies resulting from interactions with various screening orders, as described herein. As described in U.S. Pat. No. 10,916,330 B1, the total binding energy $E_{tot,Apt}=E_{SCI}+E_{HI}$, where $E_{HI}$ is the hydrophobic binding energy due to hydrophobic pull $F_{HI}$ and $E_{SCI}$ is the total binding energy due to 2 $F_{SCI}$ s. $E_{SCI}$ can be calculated as follows:

$$E_{SCI}=[(1/\varepsilon_0\varepsilon_r)q_{nu}q_{lip}]^s \exp((1/\delta_{Apt,lip})r)$$

where s is screening order to be calculated based on number of nucleotides and lipids and vice versa under SCI interactions. s=1, 2, 3, . . . , etc. for $0^{th}$ (direct Coulomb interaction), $1^{st}$, $2^{nd}$, . . . , etc. order of screening in screened Coulomb interactions. The longer the aptamer the higher is the order of screening. $q_{nu}$ and $q_{lip}$ are effective charges on a nucleotide and a lipid headgroup, respectively.

In case of liposome adsorption of aptamers, the resultant grand total/net energy of aptamer-liposome association is:

$$E_{net,Apt}=E_{tot,Apt}+E_{B,Apt}+E_{B,lip}=E_{HI}+[(1/\varepsilon_0\varepsilon_r)q_{nu}q_{lip}]^s\exp((1/\delta_{Apt,lip})r)+(k_BT/2)(1/r_{Apt/lip})^2 1_{P,Apt}-1_{Apt}/r^2+5k_BT\, a_{lip}^2/r^2$$

The net aptamer-liposome association force is:

$$F_{net,Apt}=-(d/dr)E_{net,Apt}$$

The optimal aptamer length can be determined at $r=r_0$ ($r_0$ being the optimal radius of liposome) for which $F_{net,Apt}|_{r=r0}=-(d/dr)E_{net,Apt}|_{r=r0}=0$.

Additionally, $\delta_{Apt,lip}=na_{nu}$, where $1\leq n\leq r_1/a_{nu}$ (or, $1\leq n\leq ((\pi r_1/2)/a_{nu})$). Accordingly, n is any number between 1 and a maximum value that gets determined by the size of the liposome, n is considered here to be proportional to the radius of liposome that is under the interaction with the aptamer.

As described herein, theoretical predictions about aptamer binding with a target biomolecule are made based on numerical computation of aptamer binding with lipids on a liposome. Liposomes are made of the same type of materials, i.e., various lipids, as a cell membrane. It was found that, for bigger liposomes, ABB specificity is important at low s values. At high s values, however, the specificity becomes relevant only in choosing between purine (preferred) and pyrimidine (less likely).

Selecting a corona virus envelope (CVE) size-specific aptamer can include analyzing screened Coulomb interactions (SCIs) or determining appropriate ABBs at various SCI orders (different values of s). Although ABBs at low values of s are generally nucleotide-specific, as s increases, the nucleotide specificity can be important only between the selection of purines and pyrimidines (FIGS. 3A-3D).

The SCI technique can identify aptamer lengths, thereby determining the value of n. Due to their large size, CVE aptamers are more length-specific (most important factor) than ABB-specific (less important). That said, if aptamer length is fixed (following the theoretical strategy considering the envelope size) a variety of options may be chosen from the type of nucleotides (same type or different ones) to fill in the gaps at ABB positions (at various s values). As for smaller s values, ABB specificity matters.

In an embodiment, ABBs are progressively selected with increasing s until no sensible differences among all nucleotides except purines and pyrimidines are detectable. Then, the rest of the ABB positions can be filled up with a repeating sequence of any single nucleotide member of purines or pyrimidines (or alternatively their combinations, which will further increase the aptamer numbers). Thus, purines and pyrimidines (purines favored over pyrimidines energetically) are included in specific sets of aptamers for each of the selected sequences where (for small s values) selection of ABB matters. Moreover, the length-dependent liposome binding is pronounced (aptamers with various lengths, e.g. $\frac{1}{3}^{rd}$, $\frac{2}{3}^{rd}$) and whole aptamer length from left end (ABBs closest to the target) to the right end can be chosen for the best candidate(s) aptamer.

As purines can favor the target lipid binding over pyrimidines for higher s values, it can be concluded that the choice of purine only over pyrimidine would lead to choosing the value of n smaller for a certain aptamer length, because purines are usually considered larger than pyrimidines. In this regard, a ratio of purine size: pyrimidine size can typically be 1.0:0.8 (indeed a valid assumption used in computation).

In certain embodiments of the present subject matter, aptamers may be designed from ABBs, and the ABBs may be, for example, DNA nucleotides, RNA nucleotides, or a combination thereof. One skilled in the art would understand that any other set of molecules may be suitable for the ultimate application for any biological target molecule. In the following examples and discussion, DNA or RNA nucleotides can be considered as aptamer building blocks (ABBs); i.e., DNA or RNA nucleotides, or in their combination, five nucleotides adenine, guanine, thymine, cytosine and uracil. In an embodiment, the specific aptamer length can be determined by utilizing minimum SCI binding energy conformation.

The aptamers can be theranostic (therapeutic and diagnostic) drugs to target biomolecules responsible for diseases. The biomolecules can be, for example, one or more of lipids, globular proteins, enzymes, specific amino acids, peptides, membrane proteins, DNA, and RNA. Lipids found in plasma membranes, liposomes, and viral envelopes can be responsible for various cellular diseases. In an embodiment, the biomolecules can include coronavirus envelope membrane lipids. In another embodiment, the coronavirus envelope membrane lipids can be selected from the group consisting of phosphatidylcholine (PC) and phosphatidylserine (PS).

Screened Coulomb interactions (SCIs) can facilitate aptamer design. SCIs tend to arise among polarized charges in a drug target complex. These interactions can underlie the drug target binding phenomena energetically. Thus, SCI can facilitate design of aptamers or general drugs based on information related to the aptamer and target biomolecule binding energetics.

The aptamer can be designed such that the number and sequence of the ABBs minimize SCI binding energy. For example, a target lipid nearest neighbor ABB can be chosen to be that with a minimum SCI binding energy, followed by subsequent ABBs, until subsequent aptamers add negligible SCI binding energy. In other embodiments, a set of SCI optimized aptamers of predetermined lengths (in numbers of ABBs, n) can be determined for a target according to an optimized SCI binding energy, and an aptamer can be selected by length based on an expected or known in situ environment of the target. In an embodiment, the in-situ environment can be a coronavirus envelope and the target can comprise lipids selected from the group consisting of phosphatidylcholine (PC) and phosphatidylserine (PS).

The aptamer can include multiple ABBs (at least n=2 ABBs). In some embodiments, PS is the target lipid. PS plays an important role in apoptosis. Apoptosis is a biomolecular process of programmed cell death in which PS is externalized across a cell membrane. In normal cells (non-cancerous cells), PS can exit across the cell membrane through an apoptotic region. In cancerous cells, apoptosis can be stopped, and PS migration can be distorted or stopped.

Many anticancer treatments rely on inducing apoptosis using certain therapeutic drugs. Induction of PS externalization in cancerous cells under treatment is a marker of a treatment's efficacy. A drug that binds to externalized PS may be used as a marker of anticancer drug efficacy. The lipid-binding drug may be used to quantify externalized PS and, thus, diagnose treatment stages. Such drugs are also referred to, herein, as 'diagnostic drugs.' The scenario of an externalized PS in a lipid bilayer membrane can be used as an exemplary target for designing an aptamer according to the methods described herein. The aptamer can be a PS-binding diagnostic drug.

Accordingly, an embodiment of the present subject matter relates to a method of determining efficacy of cancer treatment in a subject, the method comprising administering a therapeutically effective amount of a lipid-binding drug to a subject in need thereof, the lipid-binding drug comprising an aptamer having a sequence selected from one or more of the group consisting of GGCGGCAAAAAAAAAA (SEQ ID NO: 1), GGCGGCAAAAAAAAAAA (SEQ ID NO: 2), GGCGGCAAAAAAAAAAAA (SEQ ID NO: 3), GGCGGCAAAAAAAAAAAAA (SEQ ID NO: 4), GGCGGCGGGGGGGGGG (SEQ ID NO: 5), GGCGGCGGGGGGGGGGG (SEQ ID NO: 6), GGCGGCGGGGGGGGGGGG (SEQ ID NO: 7), GGCGGCGGGGGGGGGGGGG (SEQ ID NO: 8), CAAAGGAGCAAAAAAAAAAAAAAAAAAAAA (SEQ ID NO: 9) CAAAAGGAGCAAAAAAAAAAA-AAAAAAAAAAAA (SEQ ID NO: 10), CAAAAGG-AGCAAAAAAAAAAAAAAAAAAAAAAAA (SEQ ID NO: 11), CAAAAGGAGCAAAAAAAAAAAAAAAA-AAAAAAAAAAA (SEQ ID NO: 12), CAAAA-GGAGCGGGGGGGGGGGGGGGGGGGGGGGG (SEQ ID NO: 13), CAAAAGGAGCGGGGGGGGGGGGGGGGGG-GGGGGGGG (SEQ ID NO: 14), CAAAAGGAG-CGGGGGGGGGGGGGGGGGGGGGGGGGG (SEQ ID NO: 15), and CAAAAGGAGCGGGGGGGGGGGGGGG-GGGGGGGGGGG (SEQ ID NO:16). In an embodiment, the method can comprise binding of a fluorescent-tagged lipid-binding drug to a membrane-based lipid. In one embodiment, the membrane-based lipid can be phosphatidylserine (PS). In an embodiment, the membrane-based lipid can be externalized in a lipid bilayer membrane of a cancer cell. The binding of the fluorescent-tagged lipid-binding drug to the externalized lipid can be used as a marker to quantify externalized lipid and, thereby, diagnose efficacy of cancer drug treatment.

Computer modelling of physical laws applied on a system or process can perform computational simulations which produce almost valid in-system data. In any examples as described herein, the computer program Mathematica 9.1 (Wolfram), was used to address, in silico, the PS or PC binding of nucleic acid nucleotides adenine (A), guanine (G), thymine (T), cytosine (C), and uracil (U), or nucleic acid aptamers. Aptamers were constructed from 4 nucleotides (A, G, T, C) of deoxyribonucleic acid (DNA) or 4 nucleotides (A, G, U, C) of ribonucleic acid (RNA) or 5 nucleotides combining both DNA and RNA nucleotides. Theoretical formalism on body/charge interactions whereby charges interact in the presence of other charges through Screened Coulomb Interactions (SCIs) (Ashrafuzzaman and Tuszynslki, 2012) were considered in the calculations.

In an embodiment, a coronavirus-specific aptamer can be formed by selecting an ABB based on the charge-based interaction of the ABB and the target lipid, as set forth in U.S. Pat. No. 10,916,330 B1, the contents of which are hereby incorporated by reference in their entirety. A length of the ABB can be selected to ensure optimal binding between aptamer(s) and the lipid in general. When a chemical, e.g., an ABB, approaches a target, e.g., a lipid, individual charges on both molecular sites can polarize each other. As a result, the interactions among many polarized charges in the two-body system can be considered. The total energy in this two-body coupling can be calculated utilizing screened Coulomb interactions (SCIs) arising among many charge interactions (as set forth in U.S. Pat. No. 10,916,330 B1). The resultant binding energy can be the sum of energies resulting from interactions with various screening orders. This general theoretical formalism in EMDD can be used to design nucleic acid DNA or RNA aptamers for any biological target molecule. Chemical analysis can be used to discover the existence of electrostatic charge distributions on specific drug binding site(s) in normal physiological conditions. In certain disease cases, the charge distribution, along with the number of charges, may get distorted due to mutations. Biophysical parameterization of the charge distribution can be used to address the selection of corresponding ABBs. Accordingly, the ABBs can be both target structure and charge-distribution specific.

According to an embodiment, aptamer or drug building blocks (ABBs or DBBs) can include four DNA or RNA nucleotides, or in combination, five nucleotides, adenine, guanine, thymine, cytosine and uracil. The aptamer lengths can be determined by determining minimum SCI binding energy conformation. The target's nearest neighbor, i.e., a first ABB, can be selected based on minimum SCI binding energy condition, and subsequent ABBs can be determined by the same energetic formalism, e.g., the minimum SCI binding energy conditions for the subsequent ABB. Aptamer length can be extended based on the minimum binding energy until the total SCI binding energy allows addition of ABBs without destabilizing the binding phenomenon.

In an embodiment, aptamer length can be extended based on the biological environment hosting the TB. In a case of the coronavirus envelope, the TBs, e.g., the lipids, can exist in a bilayer membrane surrounding the envelope which can be spherical in nature and can have a diameter that is approximately 120 nm to approximately 140 nm.

According to an embodiment, the present teachings are directed to designing aptamer-based therapeutic agents or a set of candidate aptamers, to prevent or inhibit coronavirus from infecting cells.

One embodiment of the present teachings is directed to designing aptamer-based diagnostic agents, or a set of candidate aptamers, e.g., fluorescent-tagged aptamers. In one embodiment, a fluorescent-tagged aptamer can be contacted with a biological sample obtained from a patient to determine the presence of coronavirus in the biological sample, whereby binding of the fluorescent-tagged aptamers with a coronavirus envelope lipid indicates coronavirus infection in the patient.

In another embodiment, a fluorescent-tagged aptamer can be contacted with a biological sample from a cancer patient, whereby binding of the fluorescent-tagged aptamer to an externalized membrane-based lipid of a cancer cell in the biological sample can indicate efficacy of cancer drug treatment.

Exemplary aptamers were selected for in vitro liposome binding assays to address the aptamers' lipid-specific liposome binding potency. Various types of lipids, including their varied acyl chain lengths, were considered to regulate the membrane thickness and the size (diameter) of the spherical liposomes. Positive liposome adsorption of designed aptamers, due to possible aptamer-lipid binding, was observed, in general. It was determined that liposome adsorption depends on ABB specificity, but only modestly. The experimental results most importantly hinted on the liposome size requirements of aptamer lengths.

Important theoretical predictions were made based on numerical computation on aptamer binding with lipids on a liposome as described herein and U.S. Pat. No. 10,916,330. Liposomes are made of the same types of materials, i.e., various lipids, as a cell membrane. The selection of aptamers for a TB on a coronavirus envelope were made based on these computations. It was further found that the physiological condition of the buffer in which in vitro binding assays are performed also regulates the aptamer-liposome binding mechanisms.

In another embodiment, the present subject matter is directed to pharmaceutical compositions comprising a therapeutically effective amount of the at least one aptamer as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises the at least one aptamer together with at least one pharmaceutically acceptable auxiliary.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present aptamers are typically administered at a therapeutically or pharmaceutically effective dosage, e.g., a dosage sufficient to provide treatment for a coronavirus infection. Administration of the aptamers or pharmaceutical compositions thereof can be by any method that delivers the compounds systemically and/or locally. These methods include oral routes, parenteral routes, intraduodenal routes, and the like.

While human dosage levels have yet to be optimized for the present aptamers, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present aptamers for treatment of a coronavirus infection, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present aptamers can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present aptamers may also be administered as compositions prepared as foods for humans or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of the aptamer, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinyl pyrrolidine, gelatin, cellulose, and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly, or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the aptamers may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

These and other features of embodiments of the present subject matter will be further explained and demonstrated by the following examples:

EXAMPLES

Example 1

Understanding the SCI Orders

A scenario in which the distribution of liposome over radii, between smallest $r_S$ and largest $r_L$ was considered. That makes the maximum number of nucleotides in the aptamers to be not beyond $\pi r_1/a_{nu}$ or $2r_1/a_{nu}$, where $a_{nu}$ is the average distance covered by each ABB to construct an aptamer. In DNA $a_{nu} \approx 0.33$ nm which can also be considered for ABB dimension. Similarly, the maximum number of lipids that can come under SCI with aptamers in the smallest liposome is $\pi r_S/a_{lip}$ or $2r_S/a_{lip}$, where $a_{lip}$ is the average lipid head group diameter which is approximately 0.76 nm. In this special modelling of the aptamer-liposome interaction, $a_{lip} \approx 2a_{nu}$ is assumed for simplicity. The minimum number of lipids was expected to be generally falling under SCI with aptamers attempting to bind with liposome is assumed to be $\pi r_S/a_{lip} = N_{min}$ to be. The bigger the liposomes, the higher the number of lipids to experience SCI with aptamers, as in this case negligible aptamer bending would be required. The highest number of lipids under SCI with aptamers was determined to be $\pi r_1/a_{lip} = N_{max}$ beyond which the interaction will tend to be considered between aptamers and large spherical cell, not liposome. In case of aptamer-cell interactions, it was considered that aptamers get adsorbed on a two-dimensional cell surface due to aptamer length being nm order while a spherical cell's diameter is of the order of μm. So the aptamer on cell surface in fact interacts with, hypothetically, an infinite number of lipids along both directions of its length.

Example 2

Liposome Size-Specificity in Designing Aptamers

Figure 1:
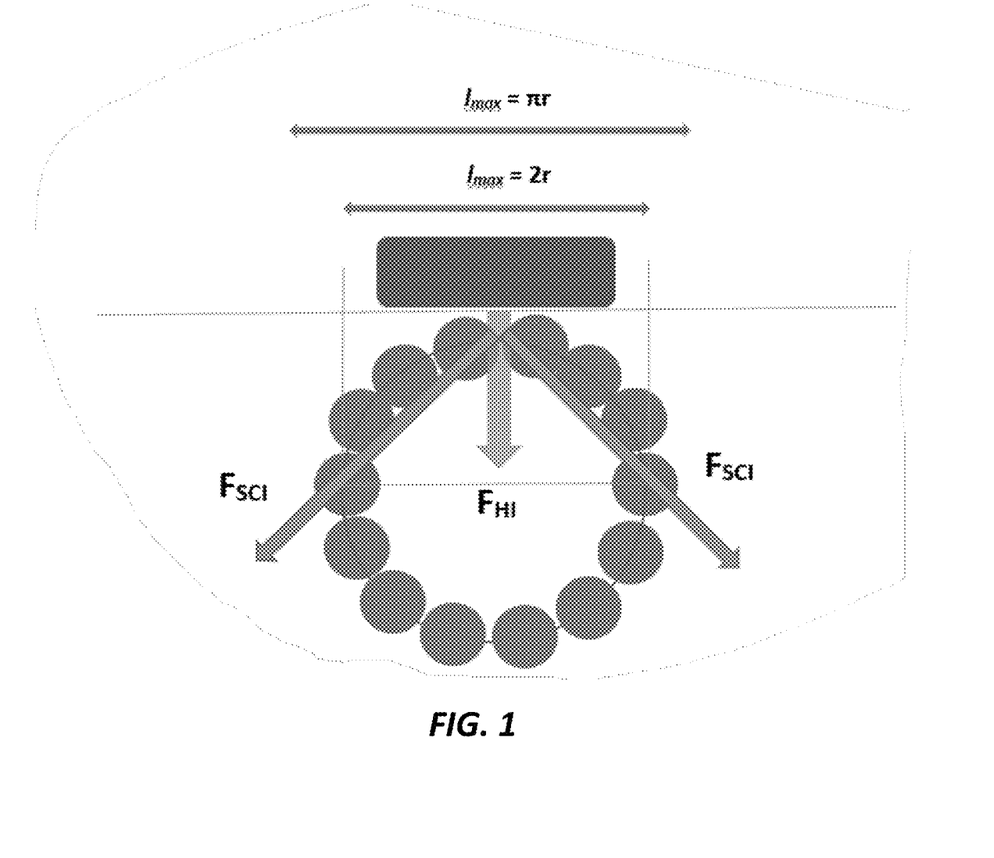
FIG. 1 is a diagram depicting aptamer length selection for a liposome with radius r.
Figure 2:
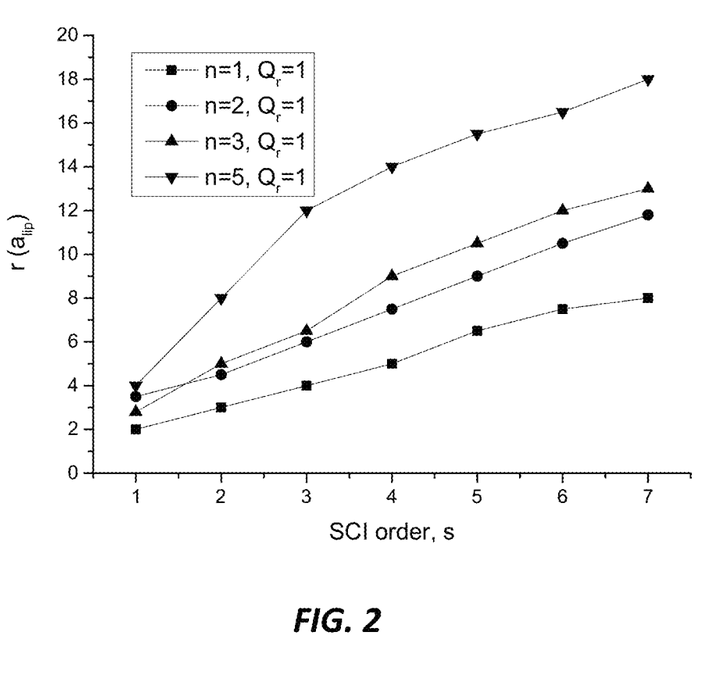
FIG. 2 is a graph showing liposome size versus SCI screening order s, specific for aptamer length of 2n ABBs, where n=3 and 5 for PS and PC aptamers, respectively, and $Q_r=1$ (curves tend to saturate as n and s increase, meaning that n and s have a mutually proportional relation).

Another scenario in which a liposome for which $2\pi r = N_{tot} \times a_{lip}$ where $N_{tot}$ is the total number of lipids across the circumference of spherical liposome is assumed. In FIG. 1, $N_{tot}=14$ where the maximum possible aptamer length, $l_{max}=\pi r=7 \times a_{lip} \approx 14\, a_{nu}$. That is in a meaningful design the aptamer may not theoretically need to consist of more than 14 nucleotides while binding with this specific size liposome.

Example 3

Liposome-Bound Aptamers

An amount of liposome-bound aptamers was detected using a NanoDrop® Microvolume Spectrophotometer (ThermoFisher Scientific®, USA) according to methods described in U.S. Pat. No. 10,916,330 B1 and Tseng, 2016. The liposomes were incubated with 100 UM aptamers in buffer. PS aptamers designed using either EFBA or SCI have short sequences for binding. This suggests that shorter PS aptamers easily bind or penetrate into the PS containing liposome having more negative curvature, e.g., more inter lipid space. For PC liposomes, the lipid curvature was zero, so both shorter and longer types of aptamers may penetrate with equal potency.

Example 4

Coronavirus Envelope Binding Aptamer

For a virion diameter=118-140 nm, a coronavirus envelope (CVE) diameter, $d_{CVE} \approx 120$ nm and CVE radius, $r_{CVE} \approx 60$ nm was assumed. Maximum length of the aptamer for CVE is $l_{max,CVE}$. That means, CVE, $l_{max}$ in FIG. 1 should be read as $l_{max,CVE}$ and r as $r_{CVE}$. As liposome size (diameter) increases, qualifying aptamer length $l_{max,CVE}$ increases (see FIG. 1). Concomitantly, ø increases up to ø90 for cell adsorption of aptamer.

Contribution of two forces were considered, namely $F_{HI}$ and $F_{SCI}$ cos ø, combination of what causes liposome surface adsorption of the aptamers.

For the same length aptamer, the liposome adsorption energy (resulting from liposome's central directed acting component $F_{HI}+F_{SCI}$ cos ø) decreases as the liposome size increases.

For bigger liposomes to ensure stable liposome adsorption of aptamers, the value of $F_{SCI}$ was increased through increasing aptamer length (what naturally causes the value of SCI order s to increase). The increasing value of $F_{SCI}$ compensates for the contribution from a decreasing value of cos ø.

It was therefore expected that shorter/longer aptamers should energetically qualify for smaller/larger liposomes, respectively.

Theoretically, it was seen that $F_{SCI}\sim\text{Exp}\ [-(1/\delta_0)\ \delta_{Apt,lip}]$. Here, as mentioned earlier, $\delta_{Apt,lip}=na_{nu}$ and $\delta_0$ is a normalizing distance, and can be considered any lattice constant $\sim a_{nu}$. The plot (not shown here) (plot $F_{SCI}$ versus $(1/\delta_0)\ \delta_{Apt,lip}$, which is nothing but the plot of $F_{SCI}$ versus n for $\delta_0=a_{nu}$) should show that $F_{SCI}$ drops exponentially with increasing n.

PC liposome size (three different sizes detected using different techniques) were: 38 nm, 80 nm, 85 nm (Ingebrigtsen and Brandl, 2002. In the theoretical techniques, the following was used:

PC aptamers: CAAAAG (SEQ ID NO: 17) (PC/SC), CAAAAGGAGC (SEQ ID NO: 18) (PC/SCI), PS aptamers: AAAGAC (SEQ ID NO: 19) (PS/EFBA)

CVE radius, $r_{CVE}\approx 60$ nm, see ref. (Payne, 2017).

According to FIG. 1, $l_{max,CVE}=\pi r_{CVE}\approx 188$ nm or, $l_{max,CVE}=2\ r_{CVE}=120$ nm.

As considered before, n is an important number that determines the number of nucleotides for constructing half of the aptamer length. Number of nucleotides in the aptamer=2n.

In DNA, the average ABB/nucleotide dimension was $a_{nu}\approx 0.33$ nm.

Therefore, the total ABB constructing aptamers with length $l_{max,CVE}$ are 2n=188/0.33 or 120/0.33=570 or 363

Or, n≈285 or 181.

From these possible values of n, the values of other related parameters can be estimated. PC liposome size, 38 nm (less accurate: 80 nm, 85 nm). Therefore, 2r=38 nm. This exactly implies for aptamers with n≈5 (see plot above), $a_{lip}\approx 1$ nm. Here, $Q_r=1$, s=7, where r starts saturating (FIG. 2). Coronavirus virion radius was $r_{CVE}\approx 60$ nm.

FIG. 2 depicts a plot of r (in unit of $a_{lip}$) versus $Q_r$. With increasing value of $Q_r$ the same aptamer (32 ABB length) may qualify for smaller envelope (n=16). Choice of ABB and charge distribution on the lipid bilayer lipid surface have considerable influence on aptamer selection.

The decreasing values of r with increasing values of $Q_r$ $(=q_{nu}/q_{lip})$, meaning either higher charges on ABB on aptamer or lower charges on lipid on envelope, may require longer aptamers for the envelope. From this finding, another conclusion may be drawn that higher charges on lipid may require shorter aptamers. This theoretical finding has been validated in our experimental assays on liposome binding of aptamers in which it was found that 6 mer aptamers are the best PS binding aptamer candidates (Tseng et al., 2011) while 10 mer aptamers are the best PC binding aptamer candidates. Therefore, the theoretical finding of 32 mer aptamers for PC and corresponding 19 mer $(2n_{CVE}=19)$ aptamers for PS on CVE made full scientific sense. Of course, the two numbers 32 and 19 mers, respectively for PC and PS on CVE, are just an estimate. The actual length of the aptamers, close to these two numbers, may not necessarily be the same.

Example 5

Selection of ABBs for PS and PC

The selection of ABBs for both PS and PC aptamers were previously described in U.S. Pat. No. 10,916,330 B1. The CVE requires aptamers covering higher s values. Therefore, additional numerical computations (NCs) were performed to determine more values of energies (covering 32 SCI orders altogether 1≤i≤32).

The energetics of transitions between energy states, suggest the following. First, the preference on selection of ABBs to construct aptamers specific for PS and PC liposomes is observed. This is the case when aptamer lengths are pretty short, experimentally validated at 2n≈6-11 among sets of candidate aptamers (see, U.S. Pat. No. 10,916,330 B1). There were 6 mer aptamers for PS, and 6 and 10 mer aptamers for PC, validated in liposome systems. As the aptamer length increased, for example to qualify for PS and PC having lipid-specific aptamer lengths with 2n≈20 and 20-32, respectively, the role of selection of ABBs became quite irrelevant. In this case, the selection of aptamer length appeared to be the most important aspect as the length proportionately increased with increasing liposome or viral envelope size.

A modest difference between energetics of aptamer binding with PS and PC was observed. This is why, perhaps the lengths of PS and PC aptamers for both types of liposomes are different. PC aptamers are longer than that of PS. For liposomes (smaller or bigger/viral envelope) a range of qualifying aptamer length for PC aptamers perhaps suggests that due to charge neutrality PC is more welcoming towards adopting quite a large set of aptamers, reflected in both small and bigger liposomes. Whereas, due to being strong negatively charged PS accommodates with a specific set of aptamers and denies others. The stress raised by membrane curvature promoted due to presence of PS is considerable, while due to PC it is nothing. This is perhaps another reason why PC is more accommodative to a wider range of aptamers on the membrane surface than PS.

It was determined that for bigger liposome or lipid envelope, the most important aspect to consider is the optimization of aptamer lengths that are compatible with the size of the liposome or lipid envelope. For smaller liposome or lipid envelope, the selection of ABBs (which modestly affects aptamer selection and binding to liposomes) is also considered.

Example 6

Lipid-ABB SCI Energetics Determines their Strength of Association

The free energy of association↔dissociation between a lipid and an ABB at $i^{th}$ order SCI, $\Delta E_{Lip,i}^{I \leftrightarrow II} = |E_{Lip,i}^{I} - E_{Lip,i}^{II}|$. The probability of Lipid-ABB association at any SCI order i follows from Boltzmann's probability function:

$p_{Lip,i} \sim \text{Exp}\{-(1/k_B T)\Delta E_{Lip,i}^{I \leftrightarrow II}\}$ Or, $-k_B T \ln p_{lip,i} \sim \Delta E_{Lip,i}^{I \leftrightarrow II}$.

Figure 3A:
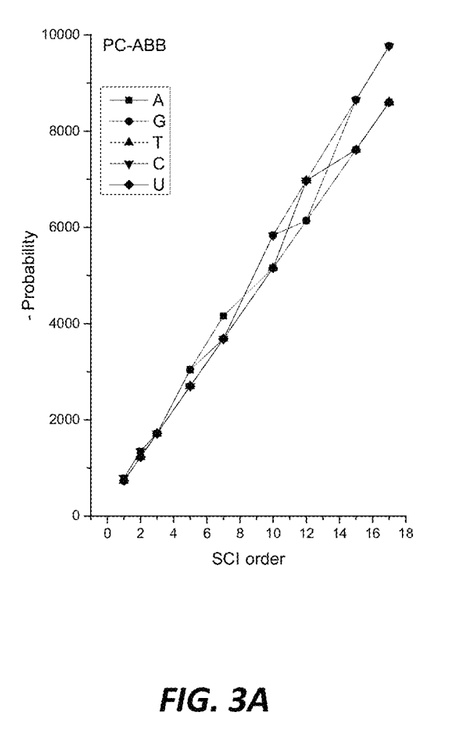
Figure 3B:
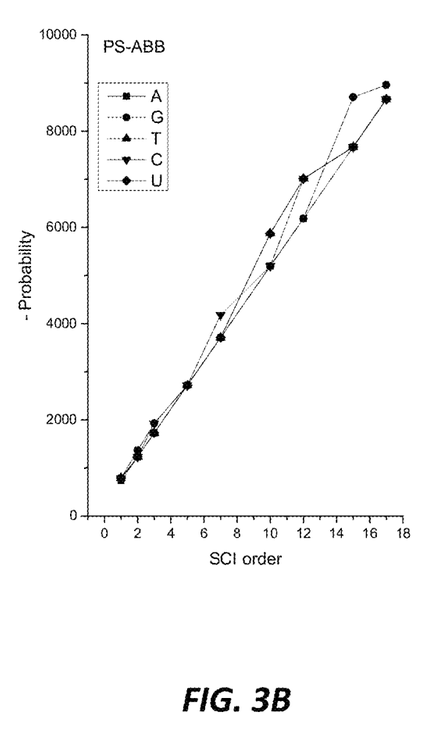
Figure 3C:
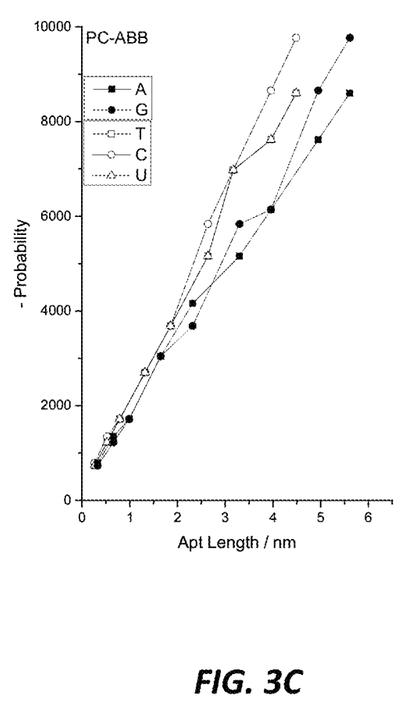
Figure 3D:
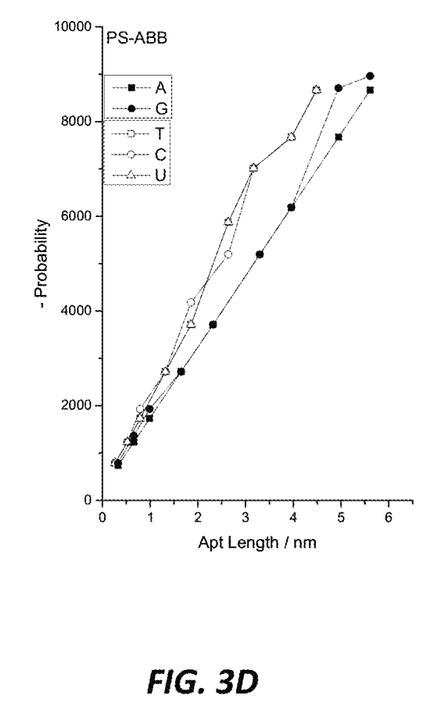
(FIG. 3D) for 5 ABBs including A and G (purines), and T, C, and U (pyrimidines) for PS (assumed ratio of purine size: pyrimidine size=1.0:0.8).

Heavier order free energetic transition $\Delta E_{Lip,i}^{I \leftrightarrow II}$ is required to add ABB at farther ends of aptamers which perhaps destabilizes the aptamer binding with lipids. The values of $-k_B T \ln p_{Lip,i}$ are generally PC or PS specific. The ABB specificity between purines and pyrimidines is found important where purines favor binding with targets over pyrimidines (FIGS. 3C-3D), although the specificity was lost among members of purines or pyrimidines. Any such preference is not detectable in FIGS. 3A-3B which consider probabilities as a function of SCI orders of ABBs. But strong ABB specificity is detectable in FIGS. 3C-3D which considers probabilities as a function of aptamer lengths. FIGS. 3C-3D, therefore, help to determine liposome specific aptamer lengths and ABB sequences, while upper panel plots fail to present the ABB sequence selection though contain information on aptamer length selection via SCI orders.

Example 7

In Vitro Experiments on Liposome Adsorption of Aptamers

To obtain an enhanced understanding of how liposome size affects aptamer adsorption mechanism, liposomes were constructed using PCs with three different acyl chain lengths, to ensure varied bilayer thickness in the liposome structure. 1,2-Dioleoyl-sn-Glycero-3-Phosphocholine ($DC_{18:1}PC$), 1,2-Diecosenoyl-sn-Glycero-3-Phosphocholine ($DC_{20:1}PC$) or 1,2-Dierucoyl-sn-Glycero-3-Phosphocholine ($DC_{22:1}PC$) (from Avanti Polar Lipids) were used that constructs bilayers with thickness ($d_0$) 47.7±2.3, 53.9±2.5 or 58.4±2.5 Å, respectively, containing hydrocarbon n-decane (Benz et al., 1975). The increasing bilayer thickness was expected to cause the liposome size to increase (also hinted in (Guha et al., 2008). As a result, the bigger liposomes were expected to also adsorb longer aptamers better.

It was observed that PS aptamers designed using either techniques EFBA or SCI are better for PS-containing liposome binding for ASS. As the sequence length increases the binding potency decreases drastically. For PC binding, aptamer length was found to be unimportant. This suggests that shorter PS aptamers perhaps easily bind or penetrate into the PS containing liposome having more negative curvature. Whereas, for PC liposome, the lipid curvature is zero. So, both shorter and longer types of aptamers may penetrate with equal potency. Of course, this hypothesis may be invalid for long aptamers which go beyond the liposome dimension.

The bilayer thickness effects on aptamer binding to liposome data hint that longer aptamers show modestly better binding with thicker bilayer (causing perhaps increasing the liposome size modestly). This suggests that the larger liposomes require longer aptamers to ensure energetically stable aptamer binding to liposome surface.

Example 8

CVE Size-Specific Design

The SCI technique can detect ABBs at various SCI orders (different values of s). Although ABBs at low values of s is very much generally nucleotide specific, as s increases, the nucleotide specificity tends to appear important only between the selection of a purines and a pyrimidine (FIGS. 3A-3D). For both PC and PS targets purines are favored over pyrimidines from energetics perspective to bind with the targets, this feature becomes clearer at higher s values. Among purines or pyrimidines there is however no considerable preferences observed. Therefore, for bigger liposomes the ABB specificity though is important at low s values, at high s values the specificity becomes relevant only in choosing between purine (preferred) and pyrimidine (less likely).

The SCI technique is quite smart in measuring the aptamer lengths, hence the value of n. Due to their large sizes, CVE aptamers are more length specific (most important factor) than ABB specific (less important). That said, if aptamer length is fixed (following the theoretical strategy presented here considering the envelope size) there are various options to choose from the type of nucleotides (same type or different ones) to fill in the gaps at ABB positions (at various s values). As for smaller s values, ABB specificity matters. It is important to consider selecting ABBs with increasing s until no differences are detected among all nucleotides but between purines and pyrimidines. Then, the rest of the ABB positions can be filled up with the repeating sequence of any single nucleotide member of purines or pyrimidines (or alternatively their combinations, which will further increase the aptamer numbers). Thus, purine and pyrimidine (purines favor over pyrimidines energetically) are included in specific sets of aptamers for each of the selected sequences where (for small s values) selection of ABB matters (see Tables 6-14 for targets PS and PC in U.S. Pat. No. 10,916,330 B1). Moreover, as length-dependent liposome binding is pronounced, aptamers with various lengths, e.g. $\frac{1}{3}^{rd}$, $\frac{2}{3}^{rd}$, and whole aptamer length from left end (ABBs closest to the target) to the right end for the best candidate(s) aptamer are selected and these three choices are tested regarding their viral envelope binding assays.

As purines are seen to favor the target lipid binding over pyrimidines for higher s values, it is also implicable that the choice of purine only over pyrimidine would lead to choosing the value of n smaller for a certain aptamer length, because purines are usually considered larger than pyrimidines, purine size: pyrimidine size=1.0:0.8 (indeed a valid assumption used in computation).

Entropic fragment based approach (EFBA) was previously used to design a few PS binding (U.S. Pat. No. 10,916,330 B1).

As an example, for the sequences where ABB selection matters most and energetics may not help distinguish among nucleotides strongly but between their purine or pyrimidine nature, the following was considered among the best aptamers for CVE: GGCGGCAAAAAAAAAA (SEQ ID NO: 1), GGCGGCAAAAAAAAAAA (SEQ ID NO: 2), GGCGGCAAAAAAAAAAAA (SEQ ID NO: 3), GGCGGCAAAAAAAAAAAAA (SEQ ID NO: 4), GGCGGCGGGGGGGGGG (SEQ ID NO: 5), GGCGGCGGGGGGGGGGG (SEQ ID NO: 6), GGCGGCGGGGGGGGGGGG (SEQ ID NO: 7), GGCGGCGGGGGGGGGGGGG (SEQ ID NO: 8), CAAAAGGAGCAAAAAAAAAAAAAAAAAAAAAAA (SEQ ID NO: 9) CAAAAGGAGCAAAAAAAAAA-AAAAAAAAAAAAAA (SEQ ID NO: 10), CAAAAG-GAGCAAAAAAAAAAAAAAAAAAAAAAAA (SEQ ID NO: 11), CAAAAGGAGCAAAAAAAAAAAAA-AAAAAAAAAAAAA (SEQ ID NO: 12), CAAAAG-GAGCGGGGGGGGGGGGGGGGGGGGGGG (SEQ ID NO: 13), CAAAAGGAGCGGGGGGGGGGGGGGGG-GGGGGGGG (SEQ ID NO: 14), CAAAAGGAGC-GGGGGGGGGGGGGGGGGGGGGGGG (SEQ ID NO: 15), and CAAAAGGAGCGGGGGGGGGGGGGGG-GGGGGGGGG (SEQ ID NO:16).

As estimated, based on special calculations 19 and 32 mers, respectively, are particularly suitable for aptamers targeting PS and PC respectively, in the coronavirus envelope (CVE).

It is to be understood that the lipid-binding drugs and methods are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

---

I claim:

1. A composition comprising:
at least one aptamer having a sequence selected from the group consisting of GGCGGCAAAAAAAAAA (SEQ ID NO: 1), GGCGGCAAAAAAAAAA (SEQ ID NO: 2), GGCGGCAAAAAAAAAAA (SEQ ID NO: 3), GGCGGCAAAAAAAAAAAA (SEQ ID NO: 4), GGCGGCGGGGGGGGGG (SEQ ID NO: 5), GGCGGCGGGGGGGGGGG (SEQ ID NO: 6), GGCGGCGGGGGGGGGGGG (SEQ ID NO: 7), GGCGGCGGGGGGGGGGGGG (SEQ ID NO: 8), CAAAAGGAGCAAAAAAAAAAAAAAAAAAAA (SEQ ID NO: 9) CAAAAGGAGCAAAAAAAAAAAAAAAAAAAAAA (SEQ ID NO: 10), CAAAAGGAGCAAAAAAAAAAAAAAAAAAAAAAAA (SEQ ID NO: 11), CAAAAGGAGCAAAAAAAAAAAAAAAAAAAAAAAAAA (SEQ ID NO: 12), CAAAAGGAGGGGGGGGGGGGGGGGGGGGG (SEQ ID NO: 13), CAAAAGGAGCGGGGGGGGGGGGGGGGGGGGGG (SEQ ID NO: 14), CAAAAGGAGCGGGGGGGGGGGGGGGGGGGGGGGG (SEQ ID NO: 15), and CAAAAGGAGCGGGGGGGGGGGGGGGGGGGGGGGGGG (SEQ ID NO:16).

2. The composition of claim 1, wherein the at least one aptamer has a sequence selected from the group consisting of GGCGGCAAAAAAAAAA (SEQ ID NO: 1), GGCGGCAAAAAAAAAA (SEQ ID NO: 2), GGCGGCAAAAAAAAAAA (SEQ ID NO: 3), GGCGGCAAAAAAAAAAAA (SEQ ID NO: 4), GGCGGCGGGGGGGGGG (SEQ ID NO: 5), GGCGGCGGGGGGGGGGG (SEQ ID NO: 6), GGCGGCGGGGGGGGGGGG (SEQ ID NO: 7), and GGCGGCGGGGGGGGGGGGG (SEQ ID NO: 8).

3. The composition of claim 1, wherein the at least one aptamer has a sequence selected from the group consisting of CAAAAGGAGCAAAAAAAAAAAAAAAAAAAA (SEQ ID NO: 9) CAAAAGGAGCAAAAAAAAAAAAAAAAAAAAAA (SEQ ID NO: 10), CAAAAGGAGCAAAAAAAAAAAAAAAAAAAAAAAA (SEQ ID NO: 11), CAAAAGGAGCAAAAAAAAAAAAAAAAAAAAAAAAAA (SEQ ID NO: 12), CAAAAGGAGGGGGGGGGGGGGGGGGGGGG (SEQ ID NO: 13), CAAAAGGAGCGGGGGGGGGGGGGGGGGGGGGG (SEQ ID NO: 14), CAAAAGGAGCGGGGGGGGGGGGGGGGGGGGGGGG (SEQ ID NO: 15), CAAAAGGAGCGGGGGGGGGGGGGGGGGGGGGGGGGG (SEQ ID NO:16).

* * * * *

SEQUENCE LISTING

```
Sequence total quantity: 19
SEQ ID NO: 1            moltype = DNA  length = 16
FEATURE                 Location/Qualifiers
source                  1..16
                        mol_type = other DNA
                        organism = synthetic construct
SEQUENCE: 1
ggcggcaaaa aaaaaa                                                    16

SEQ ID NO: 2            moltype = DNA  length = 17
FEATURE                 Location/Qualifiers
source                  1..17
                        mol_type = other DNA
                        organism = synthetic construct
SEQUENCE: 2
ggcggcaaaa aaaaaaa                                                   17

SEQ ID NO: 3            moltype = DNA  length = 18
FEATURE                 Location/Qualifiers
source                  1..18
                        mol_type = other DNA
                        organism = synthetic construct
SEQUENCE: 3
ggcggcaaaa aaaaaaaa                                                  18

SEQ ID NO: 4            moltype = DNA  length = 19
FEATURE                 Location/Qualifiers
source                  1..19
                        mol_type = other DNA
                        organism = synthetic construct
SEQUENCE: 4
ggcggcaaaa aaaaaaaaa                                                 19

SEQ ID NO: 5            moltype = DNA  length = 16
FEATURE                 Location/Qualifiers
source                  1..16
                        mol_type = other DNA
                        organism = synthetic construct
SEQUENCE: 5
ggcggcgggg gggggg                                                    16
```

-continued

```
SEQ ID NO: 6            moltype = DNA   length = 17
FEATURE                 Location/Qualifiers
source                  1..17
                        mol_type = other DNA
                        organism = synthetic construct
SEQUENCE: 6
ggcggcgggg ggggggg                                                          17

SEQ ID NO: 7            moltype = DNA   length = 17
FEATURE                 Location/Qualifiers
source                  1..17
                        mol_type = other DNA
                        organism = synthetic construct
SEQUENCE: 7
ggcggcgggg ggggggg                                                          17

SEQ ID NO: 8            moltype = DNA   length = 17
FEATURE                 Location/Qualifiers
source                  1..17
                        mol_type = other DNA
                        organism = synthetic construct
SEQUENCE: 8
ggcggcgggg ggggggg                                                          17

SEQ ID NO: 9            moltype = DNA   length = 33
FEATURE                 Location/Qualifiers
source                  1..33
                        mol_type = other DNA
                        organism = synthetic construct
SEQUENCE: 9
caaaaggagc aaaaaaaaaa aaaaaaaaaa aaa                                        33

SEQ ID NO: 10           moltype = DNA   length = 34
FEATURE                 Location/Qualifiers
source                  1..34
                        mol_type = other DNA
                        organism = synthetic construct
SEQUENCE: 10
caaaaggagc aaaaaaaaaa aaaaaaaaaa aaaa                                       34

SEQ ID NO: 11           moltype = DNA   length = 35
FEATURE                 Location/Qualifiers
source                  1..35
                        mol_type = other DNA
                        organism = synthetic construct
SEQUENCE: 11
caaaaggagc aaaaaaaaaa aaaaaaaaaa aaaaa                                      35

SEQ ID NO: 12           moltype = DNA   length = 36
FEATURE                 Location/Qualifiers
source                  1..36
                        mol_type = other DNA
                        organism = synthetic construct
SEQUENCE: 12
caaaaggagc aaaaaaaaaa aaaaaaaaaa aaaaaa                                     36

SEQ ID NO: 13           moltype = DNA   length = 33
FEATURE                 Location/Qualifiers
source                  1..33
                        mol_type = other DNA
                        organism = synthetic construct
SEQUENCE: 13
caaaaggagc gggggggggg gggggggggg ggg                                        33

SEQ ID NO: 14           moltype = DNA   length = 34
FEATURE                 Location/Qualifiers
source                  1..34
                        mol_type = other DNA
                        organism = synthetic construct
SEQUENCE: 14
caaaaggagc gggggggggg gggggggggg gggg                                       34

SEQ ID NO: 15           moltype = DNA   length = 35
FEATURE                 Location/Qualifiers
source                  1..35
                        mol_type = other DNA
                        organism = synthetic construct
SEQUENCE: 15
```

```
caaaaggagc gggggggggg gggggggggg ggggg                              35

SEQ ID NO: 16          moltype = DNA  length = 36
FEATURE                Location/Qualifiers
source                 1..36
                       mol_type = other DNA
                       organism = synthetic construct
SEQUENCE: 16
caaaaggagc gggggggggg gggggggggg gggggg                             36

SEQ ID NO: 17          moltype =     length =
SEQUENCE: 17
000

SEQ ID NO: 18          moltype = DNA  length = 10
FEATURE                Location/Qualifiers
source                 1..10
                       mol_type = other DNA
                       organism = synthetic construct
SEQUENCE: 18
caaaaggagc                                                          10

SEQ ID NO: 19          moltype =     length =
SEQUENCE: 19
000
```